United States Patent [19]

O'Neil et al.

[11] Patent Number: 5,037,568

[45] Date of Patent: Aug. 6, 1991

[54] LUBRICANT COMPOSITIONS

[75] Inventors: Robert M. O'Neil, Flixton, England; Hugo Camenzind, Fribourg, Switzerland; Kay S. Gröninger, Darmstadt, Fed. Rep. of Germany; John D. Payne, Manchester, England

[73] Assignee: CIBA-GEIGY Corporation, Ardsley, N.Y.

[21] Appl. No.: 522,630

[22] Filed: May 14, 1990

[30] Foreign Application Priority Data

May 17, 1989 [GB] United Kingdom ............... 8911287

[51] Int. Cl.$^5$ ............... C10M 133/42; C10M 135/02
[52] U.S. Cl. .................... 252/47.5; 252/34; 544/213; 544/219
[58] Field of Search ............... 544/213, 219; 252/47.5, 252/34

[56] References Cited

U.S. PATENT DOCUMENTS

| | | | |
|---|---|---|---|
| 2,836,564 | 5/1958 | Roberts et al. | 252/47.5 |
| 3,156,690 | 11/1964 | Dexter et al. | 252/47.5 |
| 3,642,630 | 2/1972 | MacPhail et al. | 252/47.5 |
| 3,819,574 | 6/1974 | Brown et al. | 260/45.8 SN |
| 3,974,162 | 8/1976 | Santilli et al. | 260/256.5 R |
| 4,038,197 | 7/1977 | Caspari | 252/47.5 |
| 4,931,196 | 6/1990 | Payne et al. | 252/47.5 |

FOREIGN PATENT DOCUMENTS

| | | |
|---|---|---|
| 0073328 | 8/1981 | European Pat. Off. . |
| 0223916 | 6/1987 | European Pat. Off. . |
| 0291236 | 11/1988 | European Pat. Off. . |
| 1176770 | 1/1970 | United Kingdom . |

Primary Examiner—Prince E. Willis
Assistant Examiner—Jerry D. Johnson
Attorney, Agent, or Firm—Luther A. R. Hall

[57] ABSTRACT

The present invention provides a lubricant composition comprising a lubricating oil and, as multifunctional additive, at least one compound having the formula I:

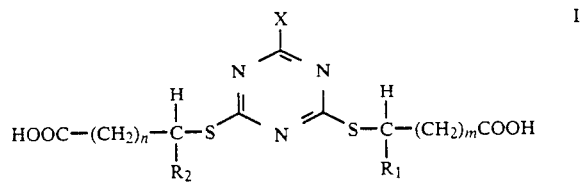

or amine salts thereof; wherein $R_1$ and $R_2$, independently, are hydrogen or methyl; n and m, independently, are 0 or 1; and X is $SR_3$ or $NR_4R_5$ wherein $R_3$ is $C_{12}$–$C_{20}$ linear or branched alkyl $R_4$ and $R_5$ are independently, $C_8$–$C_{20}$ linear or branched alkyl provided that those compounds of formula I are excluded in which m and n are each 0, X is S-$C_8$–$C_{20}$ linear or branched alkyl and $R_1$ and $R_2$ are as defined.

5 Claims, No Drawings

LUBRICANT COMPOSITIONS

The present invention relates to lubricant compositions containing multifunctional lubricant additives; to new triazine compounds; and to a new process for the production of the new triazine compounds.

The effective protection of metallic equipment from corrosion is a long standing problem. This problem is particularly acute in an environment in which ferrous metal comes into contact with a lubricant which may be contaminated with water, as in steam turbine oils.

Another problem is presented by the friction generated between rubbing metal surfaces. This results in wear and occurs, for example, on the metallic parts in an apparatus such as a hydraulic pump. In addition, under conditions of high load, breakdown of the lubricant and seizure of metallic parts may occur.

As an attempted solution to these problems, it is known that many lubricant additives will impart protection against one of corrosion, wear, extreme pressure or oxidation. However, additives which provide simultaneous protection against more than one of these phenomena are less common. In this specification, the term "multifunctional" is used to denote additives which provide both corrosion inhibiting and antiwear properties to lubricants containing them.

In U.S. Pat. No. 2,836,564 there are disclosed new reaction products of alpha-halogenated aliphatic monocarboxylic acids and 2,5-dimercapto-1,3,4-thiadiazole and their use as rust inhibitors.

In European Patent No. 223,916 there are disclosed new reaction products of alpha-halogenated half esters or amides of succinic acid and thiazole dimercaptides and their use as multifunctional lubricant additives.

In European Patent Application 291236, there are described compounds, suitable for use as extreme pressure/antiwear additives in lubricating oil compositions, having the formula:

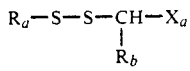

wherein $X_a$ is a carboxylic acid group, a carboxylic acid ester group, a hydroxyl group or a group $Y_aZ_a$ in which $Z_a$ is $X_a$, and $Y_a$ is alkylene, aralkylene or cycloalkene; $R_a$ is an aliphatic hydrocarbyl group; and $R_b$ is hydrogen, a hydrocarbyl group or a group $Y_aZ_a$.

We have found certain new compounds which impart superior simultaneous corrosion inhibiting and antiwear properties when incorporated into a lubricant.

Accordingly, the present invention provides a lubricant composition comprising a lubricating oil and, as multifunctional additive, at least one compound having the formula I:

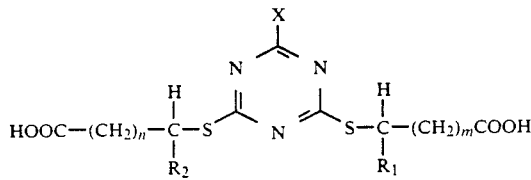

or amine salts thereof; wherein $R_1$ and $R_2$, independently, are hydrogen or methyl; n and m, independently, are 0 or 1; and X is $SR_3$ or $NR_4R_5$ wherein $R_3$ is $C_{12}$–$C_{20}$ linear or branched alkyl; $R_4$ and $R_5$, independently, are $C_8$–$C_{20}$ linear or branched alkyl, provided that those compounds of formula I are excluded in which m and n are each 0, X is S-$C_{12}$–$C_{20}$ linear or branched alkyl and $R_1$ and $R_2$ are as defined.

Preferred is a composition as described above wherein X is $NR_4R_5$ wherein $R_4$ and $R_5$ are as defined above.

The present invention also provides compounds having the formula IA:

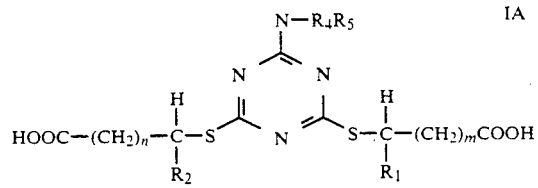

or amine salts thereof; wherein m, n, $R_1$, $R_2$, $R_4$ and $R_5$ have their previous significance.

Examples of $C_8$–$C_{20}$ linear or branched alkyl groups $R_4$ and $R_5$ include octyl, isooctyl, nonyl, decyl, undecyl, dodecyl, isododecyl, tridecyl, tetradecyl, pentadecyl, hexadecyl, isohexadecyl, heptadecyl, octadecyl, isooctadecyl, eicosyl and isoeicosyl; and 1,1,3,3-tetramethylbutyl, 2-ethylhexyl, 1-methylheptyl, 1,1,3-trimethylhexyl and trimethylundecyl.

Examples of $C_{12}$–$C_{20}$ linear or branched alkyl groups $R_3$ include the appropriate examples taken from the specific examples of $C_8$–$C_{20}$ alkyl groups $R_4$ and $R_5$.

Amine salts of compounds of formula I or IA are e.g. salts of $C_{12}$–$C_{22}$ linear or branched alkylamines such as dodecylamine, tridecylamine, tert.-tridecylamine, tetradecylamine, pentadecylamine, hexadecylamine or octadecylamine.

Specific examples of compounds of formula I (wherein X is $NR_4R_5$) and of formula IA include those summarised in the following Table:

| $R_1$ | $R_2$ | $R_4$ | $R_5$ | m | n |
|---|---|---|---|---|---|
| H | H | n-$C_8$-alkyl | n-$C_8$-alkyl | 0 | 0 |
| H | H | n-$C_9$-alkyl | n-$C_9$-alkyl | 0 | 0 |
| H | H | iso-$C_{10}$-alkyl | iso-$C_{10}$-alkyl | 0 | 0 |
| H | H | n-$C_{12}$-alkyl | n-$C_{12}$-alkyl | 0 | 0 |
| H | H | iso-$C_{13}$-alkyl | iso-$C_{13}$-alkyl | 0 | 0 |
| H | H | n-$C_{14}$-alkyl | n-$C_{14}$-alkyl | 0 | 0 |
| H | H | n-$C_{16}$-alkyl | n-$C_{16}$-alkyl | 0 | 0 |
| H | H | n-$C_{18}$-alkyl | n-$C_{18}$-alkyl | 0 | 0 |
| H | H | n-$C_{20}$-alkyl | n-$C_{20}$-alkyl | 0 | 0 |
| H | H | n-$C_8$-alkyl | n-$C_8$-alkyl | 1 | 1 |
| H | H | n-$C_{12}$-alkyl | n-$C_{12}$-alkyl | 1 | 1 |
| H | H | iso-$C_{13}$-alkyl | iso-$C_{13}$-alkyl | 1 | 1 |
| H | H | n-$C_{20}$-alkyl | n-$C_{20}$-alkyl | 1 | 1 |
| $CH_3$ | $CH_3$ | n-$C_8$-alkyl | n-$C_8$-alkyl | 0 | 0 |
| $CH_3$ | $CH_3$ | n-$C_9$-alkyl | n-$C_9$-alkyl | 0 | 0 |
| $CH_3$ | $CH_3$ | iso-$C_{10}$-alkyl | iso-$C_{10}$-alkyl | 0 | 0 |
| $CH_3$ | $CH_3$ | n-$C_{12}$-alkyl | n-$C_{12}$-alkyl | 0 | 0 |
| $CH_3$ | $CH_3$ | iso-$C_{13}$-alkyl | iso-$C_{13}$-alkyl | 0 | 0 |
| $CH_3$ | $CH_3$ | n-$C_{14}$-alkyl | n-$C_{14}$-alkyl | 0 | 0 |
| $CH_3$ | $CH_3$ | n-$C_{16}$-alkyl | n-$C_{16}$-alkyl | 0 | 0 |
| $CH_3$ | $CH_3$ | n-$C_{18}$-alkyl | n-$C_{18}$-alkyl | 0 | 0 |
| $CH_3$ | $CH_3$ | n-$C_{20}$-alkyl | n-$C_{20}$-alkyl | 0 | 0 |
| $CH_3$ | $CH_3$ | n-$C_8$-alkyl | n-$C_8$-alkyl | 0 | 0 |
| $CH_3$ | $CH_3$ | n-$C_{12}$-alkyl | n-$C_{12}$-alkyl | 1 | 1 |
| $CH_3$ | $CH_3$ | iso-$C_{13}$-alkyl | iso-$C_{13}$-alkyl | 1 | 1 |
| $CH_3$ | $CH_3$ | n-$C_{20}$-alkyl | n-$C_{20}$-alkyl | 1 | 1 |

Specific examples of compounds of formula I wherein X is $SR_3$ include those set out in the following Table:

| $R_1$ | $R_2$ | $R_3$ | m | n |
| --- | --- | --- | --- | --- |
| H | H | n-$C_{12}$-alkyl | 1 | 1 |
| H | H | iso-$C_{13}$-alkyl | 1 | 1 |
| H | H | n-$C_{14}$-alkyl | 1 | 1 |
| H | H | n-$C_{16}$-alkyl | 1 | 1 |
| H | H | n-$C_{18}$-alkyl | 1 | 1 |
| H | H | n-$C_{20}$-alkyl | 1 | 1 |
| $CH_3$ | $CH_3$ | n-$C_{12}$-alkyl | 1 | 1 |
| $CH_3$ | $CH_3$ | iso-$C_{13}$-alkyl | 1 | 1 |
| $CH_3$ | $CH_3$ | n-$C_{14}$-alkyl | 1 | 1 |
| $CH_3$ | $CH_3$ | n-$C_{16}$-alkyl | 1 | 1 |
| $CH_3$ | $CH_3$ | n-$C_{18}$-alkyl | 1 | 1 |
| $CH_3$ | $CH_3$ | n-$C_{20}$-alkyl | 1 | 1 |

Preferred compounds of formula I are those of formula IA.

The compounds of formula I or IA may be produced by a new two-stage process, which forms a further aspect of the present invention.

The first stage of the process is known, e.g. from British Patent Specification No. 1176770 and Koopman et al., Rec. Trav. Chim., 1958, 77, 235-40, and comprises the reaction of cyanuric chloride with one mole of a reactant X-H, viz. a thiol $R_3SH$ or a secondary amine $R_4R_5NH$, wherein X, $R_3$, $R_4$ and $R_5$ have their previous significance. The first reaction stage may be summarized by the following reaction scheme:

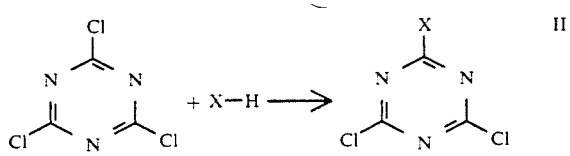

wherein X has its previous significance.

The first reaction stage is conveniently performed in the presence of an inert organic solvent e.g. a hydrocarbon such as benzene, toluene, xylene, hexane, heptane or cyclohexane; a halogenated hydrocarbon e.g. dichloromethane, chloroform or carbon tetrachloride; or an oxygenated hydrocarbon e.g. acetone or diethyl ether.

The first reaction stage is preferably conducted in the presence of a base such as an alkali metal hydroxide, especially sodium hydroxide or potassium hydroxide; ammonium hydroxide; an alkali metal carbonate, especially sodium carbonate or potassium carbonate; or an alkylamine such as triethylamine or tributylamine.

The first reaction stage may be effected preferably at 0° C. to 5° C.

The second stage of the process according to the present invention comprises reacting a compound of formula II with a mercapto acid having the formula III:

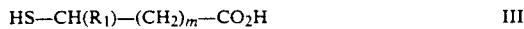
$$HS-CH(R_1)-(CH_2)_m-CO_2H \quad III$$

wherein $R_1$ and m have their previous significance and with a mercapto acid having the formula IV:

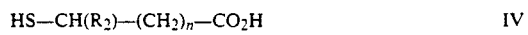
$$HS-CH(R_2)-(CH_2)_n-CO_2H \quad IV$$

wherein $R_2$ and n have their previous significance, thereby to produce a compound of formula I or IA.

Preferably the compound of formula III used, and the compound of formula IV used, are the same compound.

The second stage of the process of the present invention is preferably effected at 20° C. or below.

Conveniently, a reactant of formula II, dissolved in an inert organic solvent such as those e.g. acetone indicated for the first reaction stage, is reacted with an aqueous alkaline solution, especially solutions of sodium or potassium in form of their carbonates or hydroxides, of a compound of formula III and of a compound of formula IV.

If necessary, the second stage reaction may be effected in the presence of a phase transfer catalyst e.g. tetraalkylammonium halide.

The ratio of reactant II to reactant III may range from 1:2 to 2:5. The ratio of reactant II to reactant IV may range from 1:2 to 2:5.

The reaction mixture may then be heated under reflux for several hours. Upon cooling, the reaction mixture may be acidified and the product isolated in conventional manner e.g. by filtration, or solvent extraction and subsequent evaporation. The crude product may be purified by customary techniques such as recrystallisation or chromatography e.g. on silica gel.

The compounds of formula I are active in imparting desirable properties to lubricants. They are particularly effective as corrosion inhibitors and antiwear agents. The said compounds are effective in amounts of e.g. 0.01-5 wt %, especially 0.02-1 wt % based on the lubricant.

Preferred are lubricant compositions wherein the lubricating oil is a turbine oil or a hydraulic oil.

The lubricating oil may be a mineral oil, a synthetic oil or any mixture of such oils. Mineral oils are preferred and examples of these include paraffinic hydrocarbon oils e.g. a mineral oil having a viscosity of 46 $mm^2/s$ at 40° C.; "150 Solvent Neutral" a solvent refined neutral mineral oil having a viscosity of 32 $mm^2/s$ at 40° C.; and "solvent bright-stocks", a high boiling residue from the process of refining mineral oil, and having a viscosity of 46 $mm^2/s$ at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula:

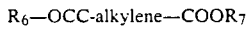
$$R_6-OCC-alkylene-COOR_7$$

wherein "alkylene" denotes an alkylene residue having from 2 to 14 carbon atoms and $R_6$ and $R_7$ are the same or different and each is an alkyl group having from 6 to 18 carbon atoms. Tri-esters which are of use as lubricating oil base stocks are those derived from trimethylolpropane and $C_6-C_{18}$ mono-carboxylic acids or mixtures thereof, whereas suitable tetra-esters include those derived from pentaerythritol and a $C_6-C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from an aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoffe und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

EXAMPLES OF PHENOLIC ANTIOXIDANTS

1. Alkylated Monophenols 2,6-Di-tert-butyl-4-methylphenol, 2,6-di-tert-butylphenol, 2-tert-butyl-4,6-dimethylphenol, 2,6-di-tert-butyl-4-ethyl-phenol, 2,6-di-tert-butyl-4-n-butylphenol, 2,6-di-tert-butyl-4-i-butylphenol, 2,6-di-cyclopentyl-4-methylphenol, 2-(β-methylcyclohexyl)-4,6-dimethylphenol, 2,6-di-octa-decyl-4-methylphenol, 2,4,6-tricyclohexylphenol, 2,6-di-tert-butyl-4-methoxymethyl-phenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexyl-phenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl)-4-nonylphenol), 2,2'-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxy-benzyl)-4-methylphenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)-dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acrylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenol)-propionic acid with mono- or polyhydric alcohols, for example with methanol, diethyleneglycol, octadecanol, triethyleneglycol, 1,6-hexane-diol, pentaerythritol, neopentylglycol, tris-hydroxyethyl-isocyanurate, thiodiethyleneglycol, bis-hydroxyethyl-oxalic acid diamide.

8. Esters of β-(5-tert-butyl-4-hydroxy-3-methylphenyl)-propionic acid with mono- or polyhydric alcohols, for example with methanol, diethyleneglycol, octadecanol, triethyleneglycol, 1,6-hexane-diol, pentaerythritol, neopentylglycol, tris-hydroxyethyl-isocyanurate, thiodiethyleneglycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexamethylenediamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of amine antioxidants

N,N'-Di-isopropyl-p-phenylenediamine, N,N'-di-sec.-butyl-p-phenylene-diamine, N,N'-bis(1,4-dimethylpentyl)-p-phenylene-diamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethylbutyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldiphenylamine, 4-isopropoxy-diphenylamine, N-phenyl-1-naphthyl-amine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoylamino-phenol, 4-octadecanoyl-amino-phenol, di-(4-methoxy-phenyl)-amine, 2,6-di-tert-butyl-4-dimethyl-amino-methyl phenol, 2,4'-diamino-diphenylmethane, 4,4'-diamino-diphenyl-methane, N,N,N',N'-tetramethyl-4,4'-diamino-diphenylmethane, 1,2-di-(phenylamino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, n-allylphenothiazine.

Examples for other antioxidants

Aliphatic or aromatic phosphites, esters of thiodipropionic acid or of thiodiacetic acid, or salts of dithiocarbamic or dithiophosphoric acid.

Examples of metal passivators, for example for copper, are

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicylidene-propylene-diamine and salicyclamino-guanidine and salts thereof, 1,2,4-triazole and N,N'-disubstituted aminomethyl triazoles of formula

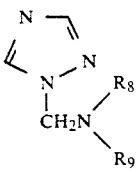

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are (a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.

(b) Nitrogen-containing compounds, e.g.

I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.

(c) Phosphorus-containing compounds, e.g.

amine salts of phosphonic acid or phosphoric acid partial esters, zinc dialkyldithio phosphates.

(d) Sulfur-containing compounds, e.g.

barium-dinonylnaphthalene-n-sulfonates, calcium petroleum sulfonates.

(e) Derivatives of gamma-alkoxypropylamines described in Japanese Patent Publication No. 15783/1973; and (f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y-NH_2$ with an acid $R_{10}CO_2H$, as disclosed in DE-OS 34 37 876 (German Offenlegungsschrift).

(g) Compounds having the formula $$R_{12}-X_2-CH_2-CH(OH)-CH_2NR_{13}R_{14}$$

in which $X_2$ is $-O-$, $-S-$, $-SO_2-C(O)-O-$ or $-N(Rd)$ in which $R_{12}$ is H or $C_1-C_{12}$ alkyl, $R_{13}$ is unsubstituted $C_1-C_4$ alkyl or $C_2-C_5$ alkyl substituted by one to three hydroxyl groups, $R_{14}$ is hydrogen, unsubstituted $C_1-C_4$ alkyl or $C_2-C_5$ alkyl substituted by one to three hydroxyl groups provided that at least one of $R_{13}$ and $R_{14}$ is hydroxy-substituted, and $R_{12}$ is $C_2-C_{20}$ alkyl $-CH_2-CH(OH)-CH_2NR_{13}R_{14}$ or $R_{12}$ is $C_2-C_{18}$ alkenyl, $C_2-C_3$ alkynyl or $C_5-C_{12}$ cycloalkyl provided that, when $X_2$ is $-O-$ or $-C(O)-O-$, $R_{12}$ is branched $C_4-C_{20}$ alkyl. These compounds are described in GB Patent Specification 2172284A.

(h) Compounds having the formula:

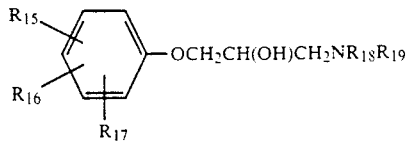

in which $R_{15}$, $R_{16}$, $R_{17}$ are, independently, hydrogen, $C_1-C_{15}$ alkyl, $C_5-C_{12}$ cycloalkyl, $C_6-C_{15}$ aryl or $C_7-C_{12}$ aralkyl and $R_{18}$ and $R_{19}$, independelty, are hydrogen, 2-hydroxyethyl or 2-hydroxypropyl, provided that $R_{18}$ and $R_{19}$ are not simultaneously hydrogen and, when $R_{18}$ and $R_{19}$ are each $-CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are

Polyacrylates, polymethacrylates, vinylpyrrolidone-meth-acrylate-copolymers, polyvinylpyrrolidones, polybutanes, olefin-copolymers, styrene/-acrylate-copolymers, polyethers.

Examples of pour-point depressants are

Polymethacrylates, alkylated naphthalene derivatives.

Examples of dispersants/detergents are

Polybutenylsuccinic acid-amides or -imides, polybutenyl-phosphonic acid derivatives, basic magnesium-, calcium-, and bariumsulfonates and -phenolates.

Examples of anti-wear additives and extreme pressure additives are

Sulphur- and/or phosphorus- and/or halogen-containing compounds e.g sulphurised vegetable oils, zinc dialkyldithiophosphates, tritolylphosphate, chlorinated paraffins, alkyl- and aryldi- and trisulphides, triphenylphosphorothionate.

The present invention also includes a process of improving the corrosion inhibiting and antiwear properties of lubricating oils by incorporation of at least one compound of formula I or an amine salt thereof, as mentioned above, into said lubricant.

Further, the present invention includes the use of at least one compound of formula I or an amine salt thereof, as mentioned above, in a lubricating oil in order to improve the corrosion inhibiting and antiwear properties thereof.

The following Examples further illustrate the invention:

In these Examples, all parts and percentages given are by weight unless otherwise specified.

EXAMPLE 1

(A)

2-Hexadecylmercapto-4,6-bis(carboxymethylmercapto)-1,3,5-triazine 4,6-Dichloro-2-hexadecylmercapto-1,3,5-triazine (20.3 g; 0.05 mole) is dissolved in acetone (200 ml). The stirred solution is cooled to 10° C. and treated, dropwise, over 30 minutes with a solution of mercaptoacetic acid (9.2 g; 0.1 mole) in water (50 ml) containing potassium carbonate (13.8 g; 0.1 mole).

After complete addition, the mixture is then heated to reflux and maintained at this temperature for 3 hours.

The mixture is then cooled to ambient temperature and acidified with dilute hydrochloric acid. The resulting cream coloured precipitate is filtered off, washed with water, dried under vacuum, and finally, recrystallised from ethanol.

The product is obtained as a cream coloured powder, yield=23.0 g (89%) mp=151° C.

Analysis: Found: C, 53.46%; H, 7.83%; N, 7.83%.
$C_{23}H_{39}N_3O_4S_3$: Requires: C, 53.35%; H, 7.59%; N, 8.11%.

(B)

2-Hexadecylmercapto-4,6-bis(carboxymethylmercapto)-1,3,5-triazine-bis tert.-tridecylamine salt.

This product is obtained by gently warming together the product of Example 1(A) with 2 molar equivalents of tert-tridecylamine. The product is obtained as a pale yellow viscous oil.

EXAMPLE 2

(A)

2-Dodecylmercapto-4,6-bis(2-carboxyethyl-mercapto)-1,3,5-triazine is synthesised from 4,6-dichloro-2-dodecyl-mercpato-1,3,5-triazine and 3-mercaptopropionic acid by the same method as outlined in Example 1(A). Yield=98% mp=122° C.

Analysis: Found: C, 51.37%; H, 7.32%; N, 8.40%.
$C_{21}H_{35}N_3O_4S_3$: Requires: C, 51.50%; H, 7.20%; N, 8.58%.

(B)

2-Dodecylmercapto-4,6-bis(2-carboxyethylmercapto)-1,3,5-triazine-bis tert-tridecylamine salt.

This product is obtained by gently warming together the product of Example 2(A) with 2 molar equivalents of tert-tri-decylamine. The product is obtained as a pale yellow viscous oil.

The following additional products of formula (I) are synthesised by similar methods to those outlined in Example 1.

| Example | X | $R_1/R_2$ | n | mp | yield |
|---|---|---|---|---|---|
| 3 | $SC_{16}H_{33}$ | H | 1 | 132° C. | 91% |
| 4 | $SC_{18}H_{37}$ | H | 1 | 129° C. | 41% |

The following bis-amine salts of products of formula (I) were also synthesised.

| Example | Product of Example | Amine | mp |
|---|---|---|---|
| 5 | 3 | tert $C_{13}H_{27}NH_2$ | viscous oil |
| 6 | 4 | tert $C_{13}H_{27}NH_2$ | viscous oil |

EXAMPLE 7

2-Ditridecylamino-4,6-bis(carboxymethylmercapto)-1,3,5-triazine 4,6-Dichloro-2-ditridecylamino-1,3,5-triazine (15.9 g; 0.03 mole) is dissolved in acetone (150 ml) and treated dropwise with a solution of 2-mercaptoacetic acid (6.8 g; 0.072 mole) in 78 ml 2N sodium hydroxide.

After complete addition, tetrabutylammonium bromide (4 g) is added to the mixture and the mixture is heated under reflux for 6 hours, whereupon two layers are formed.

The mixture is cooled to ambient temperature and acifidied with dilute hydrochloric acid. The mixture is then extracted into ethyl acetate, the extract washed with brine and with water and finally, concentrated to dryness under reduced pressure. Excess 2-mercaptoacetic acid is removed under vacuum and the crude product is purified by chromatography on silica gel, eluting with toluene then ethyl acetate. The eluate is concentrated to dryness under vacuum to yield the product as a viscous yellow oil (8.4 g; 42%).

Analysis: Found: C, 61.94%; H, 9.57%; N, 8.57%.
$C_{33}H_{60}N_4O_4S_2$: Requires: C, 61.84%; H, 9.44%; N, 8.74%.

EXAMPLE 8

2-Ditridecylamino-4,6-bis(2-carboxyethylmercapto)-1,3,5-triazine is synthesised from 4,6-dichloro-2-ditridecyl-amino-1,3,5-triazine and 3-mercapto-propionic acid by the same method as outlined in Example 7. Yield=53% viscous off-white oil.

Analysis: Found: C, 63.50%; H, 9.94%; N, 8.27%.
$C_{35}H_{64}N_4O_4S_2$: Requires: C, 62.83%; H, 9.64%; N, 8.37%.

Using the same method outlined in Example 8, the following further products are obtained.

| Example | X | $R_1/R_2$ | n | Yield | Description | Found C | Analysis H | Theoretical N % |
|---|---|---|---|---|---|---|---|---|
| 9 | $-N(C_{13}H_{27})_2$ | $CH_3$ | 0 | 39% | viscous off-white oil | 63.45 / 62.83 | 9.81 / 9.64 | 8.22 / 8.37 |
| 10 | $-N(C_{18}H_{37})_2$ | $CH_3$ | 0 | 87% | viscous off-white oil | 67.18 / 66.78 | 10.66 / 10.46 | 6.95 / 6.92 |
| 11 | $-N(C_{18}H_{37})_2$ | H | 1 | 70% | white crystals mp 97-9° C. | 66.29 / 66.78 | 10.28 / 10.46 | 6.96 / 6.92 |
| 12 | $-N(C_{18}H_{37})_2$ | H | 0 | 73% | white crystals mp 102-4° C. | 65.83 / 66.11 | 10.10 / 10.32 | 7.36 / 7.17 |

EXAMPLES 13 TO 22

The rust inhibiting and antiwear properties of the compounds of the invention are determined by the following methods.

Rust Inhibition-ASTM D665B Test

Several of the products used according to the present invention are tested as rust inhibitors in a turbine grade oil of viscosity 26.2 mm²/s at 40° C., 4.8 mm²/s at 100° C. and sulphur content of 0.54%, using the ASTM D665B method. The test results are expressed in the following manner.

Rating

0 - No rust or traces of rust on test spindle

1 - Rusting confined to not more than 6 spots, each of which is 1 mm or less in diameter 2 - Rusting in excess of the above but confined to less than 5% of the surface of the spindle 3 - Rusting covering more than 5% of the surface of the spindle.

| Example | Product of Example No. | Concentration | Test Result |
|---------|-----------------------|---------------|-------------|
| —       | Blank (no additive)   | —             | 3           |
| 13      | 1B                    | 0.10%         | 0           |
| 14      | 2B                    | 0.10%         | 0           |
| 15      | 5                     | 0.10%         | 0           |
| 16      | 6                     | 0.10%         | 0           |
| 17      | 7                     | 0.05%         | 0           |
| 18      | 8                     | 0.05%         | 0           |
| 19      | 9                     | 0.05%         | 0           |
| 20      | 10                    | 0.05%         | 0           |
| 21      | 11                    | 0.05%         | 0           |
| 22      | 12                    | 0.05%         | 0           |

EXAMPLES 23 TO 30

Antiwear Properties (IP239 Test) The method using the four-ball apparatus is employed to test for suitability for antiwear protection. Using this method, the average wear scar diameter (WSD) at a load of 40 kg for 1 hour is measured.

The tests are caried out on several of the products of the invention dissolved in a turbine grade oil of viscosity 26.2 mm²/s at 40° C., 4.8 mm²/s at 100° C. and sulphur content of 0.54%.

| Example | Product of Example No. | WSD (mm) Concentration | | | |
|---------|-----------------------|-------|-------|-------|-------|
|         |                       | 0.05% | 0.25% | 0.05% | 1.0%  |
| 23      | 1B                    | —     | —     | 0.83  | 0.75  |
| 24      | 2B                    | —     | 0.70  | —     | 0.80  |
| 25      | 7                     | 0.57  | 0.68  | —     | 0.73  |
| 26      | 8                     | 0.57  | 0.64  | —     | 0.70  |
| 27      | 9                     | 0.56  | 0.65  | —     | 0.73  |
| 28      | 10                    | 0.56  | 0.63  | —     | 0.71  |
| 29      | 11                    | 0.58  | 0.63  | —     | 0.68  |
| 30      | 12                    | 0.59  | 0.64  | —     | 0.74  |

A blank (the base oil alone) gives a WSD of 1.00 mm.

What is claimed is:

1. A lubricant composition comprising a lubricating oil and, as multifunctional additive, at least one compound having the formula I:

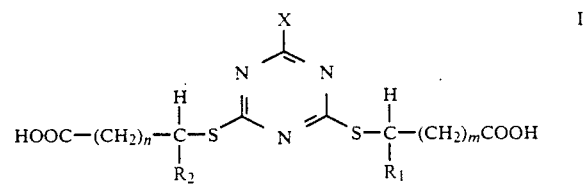

or amine salt thereof; wherein $R_1$ and $R_2$, independently, are hydrogen or methyl; n and m, independently, are 0 or 1; and X is $NR_4R_5$ wherein $R_4$ and $R_5$ independently, are $C_8$–$C_{20}$ linear or branched alkyl.

2. A composition according to claim 1 wherein the amount of the compound of formula I present ranges from 0.01 to 5 weight percent, based on the weight of the lubricant.

3. A composition according to claim 1 wherein the lubricating oil is a turbine oil or a hydraulic oil.

4. Method of improving the corrosion inhibiting and antiwear properties of a lubricating oil by incorporating into said oil at least one compound of formula I or an amine salt thereof according to claim 1.

5. A compound having the formula IA

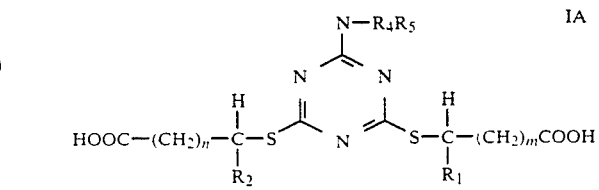

or an amine salt thereof;
wherein
$R_1$ and $R_2$ are independently hydrogen or methyl;
n and m are independently 0 or 1; and
$R_4$ and $R_5$ are independently $C_8$–$C_{20}$ linear or branched alkyl.

* * * * *